US012496188B2

(12) United States Patent
Singh et al.

(10) Patent No.: US 12,496,188 B2
(45) **Date of Patent: *Dec. 16, 2025**

(54) RETRACTABLE CAP ACTUATION FOR AN INTRAOCULAR LENS CARTRIDGE

(71) Applicant: Alcon Inc., Fribourg (CH)

(72) Inventors: Sudarshan B. Singh, Euless, TX (US); Todd Taber, Keller, TX (US); Yinghui Wu, Cedar Hill, TX (US); Douglas Brent Wensrich, Bedford, TX (US); Sam Jang, Woodbury, MN (US); Chris Pinkham, St. Paul, MN (US)

(73) Assignee: Alcon Inc., Fribourg (CH)

( * ) Notice: Subject to any disclaimer, the term of this patent is extended or adjusted under 35 U.S.C. 154(b) by 274 days.

This patent is subject to a terminal disclaimer.

(21) Appl. No.: 18/486,110

(22) Filed: Oct. 12, 2023

(65) Prior Publication Data

US 2024/0033074 A1 Feb. 1, 2024

Related U.S. Application Data

(63) Continuation of application No. 16/999,449, filed on Aug. 21, 2020, now Pat. No. 11,833,032.

(60) Provisional application No. 63/048,325, filed on Jul. 6, 2020, provisional application No. 62/890,859, filed on Aug. 23, 2019.

(51) Int. Cl.
*A61F 2/16* (2006.01)

(52) U.S. Cl.
CPC ............ *A61F 2/1678* (2013.01); *A61F 2/167* (2013.01)

(58) Field of Classification Search
CPC .................... A61F 2/167; A61F 2/1678; A61F 2002/1683; A61F 2/1664; A61F 2/1672
See application file for complete search history.

(56) References Cited

U.S. PATENT DOCUMENTS

| | | | | |
|---|---|---|---|---|
| 6,386,357 | B1 * | 5/2002 | Egawa | A61F 2/1664 606/1 |
| 2002/0077633 | A1 | 6/2002 | Kikuchi et al. | |
| 2007/0150055 | A1 | 6/2007 | Pynson | |
| 2018/0271647 | A1 | 9/2018 | Mueller | |
| 2019/0105151 | A1 * | 4/2019 | Tseng | A61F 2/1691 |

FOREIGN PATENT DOCUMENTS

| | | | |
|---|---|---|---|
| JP | H10309294 | A | 11/1998 |
| WO | 2018130940 | A1 | 7/2018 |

* cited by examiner

*Primary Examiner* — Ashley L Fishback
*Assistant Examiner* — Chima U Igboko
(74) *Attorney, Agent, or Firm* — Patterson + Sheridan, LLP

(57) ABSTRACT

Systems, methods, and apparatuses for removably attaching a drive mechanism handpiece to an intraocular lens (IOL) cartridge that folds the IOL upon retraction of a cap, are provided. The IOL cartridge comprises a nozzle and a compartment configured to receive an IOL. The nozzle is in fluid communication with the compartment. The IOL cartridge also includes a retractable cap that covers the nozzle and the compartment. The retractable cap is configured to expose the nozzle and fold the IOL upon retraction of the retractable cap. The IOL cartridge may also include a plunger case that is in fluid communication with the compartment, wherein a plunger is movably disposed within the plunger case.

19 Claims, 7 Drawing Sheets

RETRACTABLE CAP ACTUATION FOR AN INTRAOCULAR LENS CARTRIDGE

CROSS-REFERENCE TO RELATED APPLICATION(S)

This application is a continuation of U.S. Non-Provisional patent application Ser. No. 16/999,449, filed Aug. 21, 2020, which claims priority to and benefit of U.S. Provisional Patent Application No. 63/048,325, filed Jul. 6, 2020, and U.S. Provisional Patent Application No. 62/890,859, filed Aug. 23, 2019. The entire contents of each of which are incorporated by reference herein in their entirety.

TECHNICAL FIELD

The present disclosure generally relates to eye surgery and, more particularly, some embodiments may generally relate to systems, methods, and apparatuses for removably attaching a drive mechanism handpiece to an intraocular lens (IOL) cartridge that folds the IOL upon retraction of a cap.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery.

For cataract surgery, a surgical procedure may require incisions and insertion of tools within an eye to replace the clouded lens with an IOL. An insertion tool can be used for delivery of the IOL into the eye. By way of example, the insertion tool may include a plunger for forcing the IOL out of the nozzle of the insertion tool. In some instances, the IOL may be preloaded in the insertion tool. In other instances, a separate compartment may be loaded into the insertion tool. The plunger may engage the IOL to advance the IOL from the compartment, through a nozzle, and into the eye.

SUMMARY

In an exemplary embodiment, the present disclosure provides an intraocular lens (IOL) cartridge that folds the IOL upon retraction of a cap. The IOL cartridge comprises a nozzle and a compartment configured to receive an IOL. The nozzle is in fluid communication with the compartment. The IOL cartridge also includes a retractable cap configured to be retracted from a first position to a second position to manipulate the IOL for delivery and to expose the nozzle. The IOL cartridge may also include a plunger case that is in fluid communication with the compartment, wherein a plunger is movably disposed within the plunger case. The IOL cartridge may be configured such that when the retractable cap is in the first position, the nozzle is positioned within the cap, and when the cap is in the second position, the nozzle is at least partially exposed outside of a distal end of the cap.

In another exemplary embodiment, the present disclosure provides an IOL cartridge comprising a housing and a cap. The housing may comprise a compartment configured to receive an IOL. The cap may be adapted to at least partially surround the compartment and be configured to be retracted from a first position to a second position to actuate a folding mechanism of the housing to manipulate an IOL for delivery. The folding mechanism may comprise a first set of actuators, and the cap may comprise a first set of internal ramps configured to actuate the first set of actuators as the cap is retracted from the first position to the second position. The first set of actuators may include a pair of edge roller pivotably attached to the housing and configured to contact the first set of internal ramps. The folding mechanism may further comprise a second set of actuators, and the cap may further comprise a second set of internal ramps configured to actuate the second set of actuators as the cap is retracted from the first position to the second position. The second set of actuators may include a pair of compression arms pivotably attached to the housing and configured to contact the second set of internal ramps.

In another exemplary embodiment, the present disclosure provides a method for delivery of an IOL into an eye. The method comprises attaching an IOL cartridge to a handpiece. The IOL cartridge comprises a nozzle and a compartment comprising an IOL. The nozzle is in fluid communication with the compartment. The IOL cartridge also includes a retractable cap that covers the nozzle and the compartment. The IOL cartridge may also include a plunger case that is in fluid communication with the compartment, wherein a plunger is movably disposed within the plunger case. The method further includes retracting the retractable cap to expose the nozzle and fold the IOL.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
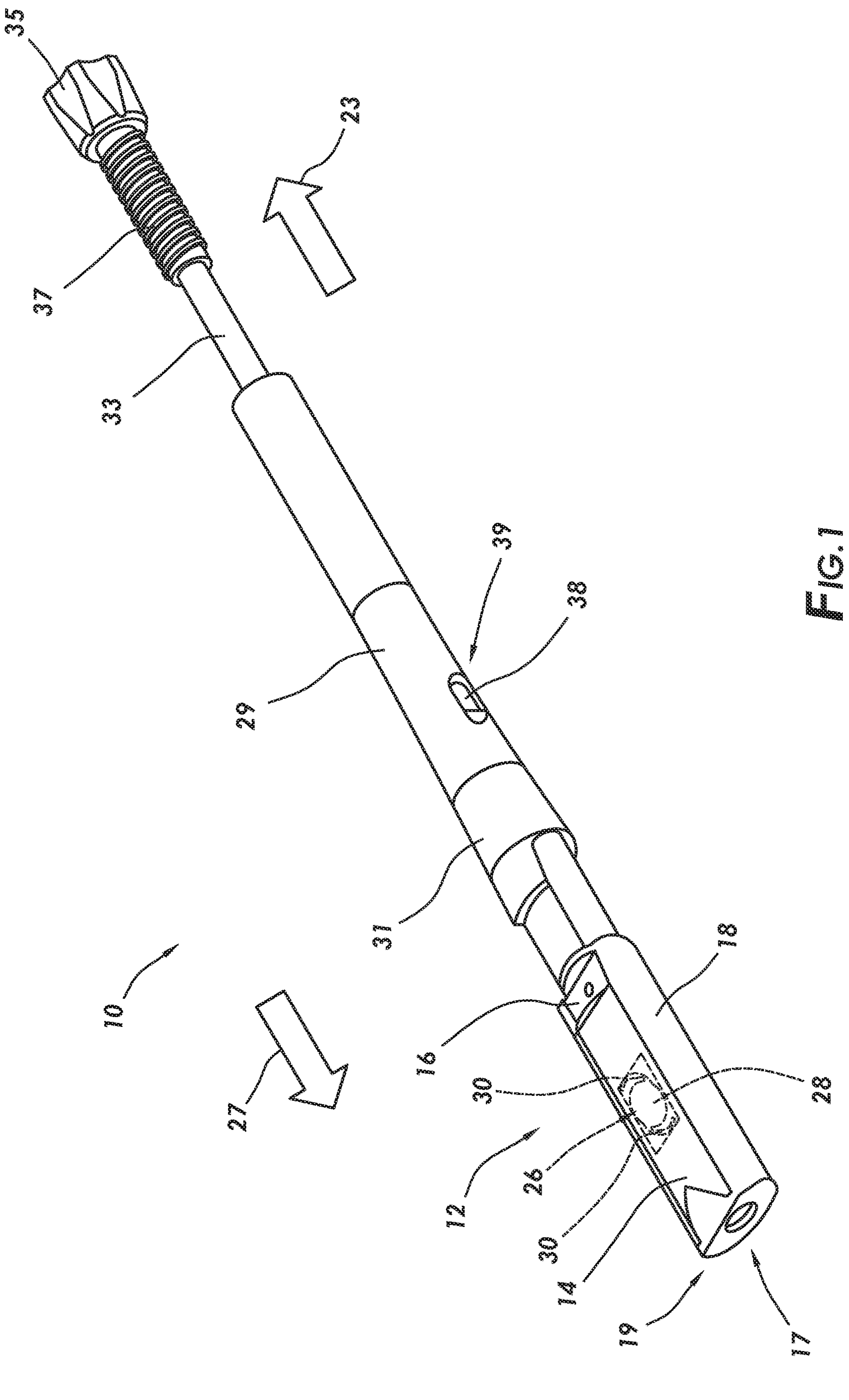
FIG. 1 illustrates a top perspective view of an insertion tool including an IOL cartridge with a retractable cap in an initial non-retracted position, in accordance with some embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments of the present disclosure provide an intraocular lens cartridge ("IOL cartridge") that folds the IOL upon retraction of a cap. The cap may initially cover, in a non-retracted position, a nozzle of the IOL cartridge to protect the nozzle from any damage during storage and/or shipping. Retracting the cap exposes the nozzle and also actuates a folding mechanism of the IOL cartridge to fold the IOL for delivery into an eye. The IOL cartridge may be a preloaded cartridge that is preloaded with the IOL. The IOL cartridge may be part of a modular delivery system that includes a universal interface for removable attachment to various handpieces that include different types of drive mechanisms.

Particular embodiments of the present disclosure allow interchangeability between different handpieces such as disposable and reusable handpieces, and the IOL cartridge. The disposable handpieces may include manual drive mechanisms (e.g., manually actuated via pushing or screwing, and/or manually actuated via a fluid or a resilient member such as a spring) that are not electrically powered. The reusable handpieces may include the manual drive mechanisms as well as electrically powered drive mechanisms (e.g., stator windings). It should be noted that these types of handpieces are examples and that other types of handpieces or drive mechanisms may be utilized in accordance with particular embodiments of the present disclosure.

Particular embodiments of the present disclosure allow assembling of the handpiece to the IOL cartridge, delivering the IOL, and disengaging the handpiece from the used IOL cartridge, if needed. The universal interface allows the different types of handpieces to be easily paired to and utilized with the IOL cartridge for IOL implantation. A handpiece may be secured to the IOL cartridge by sliding an end of the handpiece over the plunger case of the IOL cartridge to form an insertion tool. Once the insertion tool is formed, the IOL may be delivered into an eye. After the IOL implantation, the IOL cartridge can be easily detached from the handpiece (e.g., a reusable handpiece) by pulling the handpiece from the IOL cartridge.

FIG. 1 illustrates a top perspective view of an insertion tool 10 including an IOL cartridge 12 with a retractable cap ("cap") 14 in an initial non-retracted position, in accordance with some embodiments of the present disclosure. In the illustrated embodiment, the cap 14 may be movably disposed over an interior housing 16 of the IOL cartridge 12. The interior housing 16 may house a compartment 18. An IOL 26 may be disposed within the compartment 18.

The IOL 26 may be any suitable intraocular lens. The IOL 26 may include a lens portion 28 and haptic extensions 30. The haptic extensions 30 may be side struts (or other suitable extensions) extending from the lens portion 28 that may stabilize the IOL 26 when it may be disposed within the patient's eye. It should be understood that the IOL 26 shown in FIG. 1 is merely exemplary and that techniques disclosed herein may be used with any suitable IOL. For example, a modular IOL (not shown) that includes a lens portion disposable in a base with haptic extensions can also be used.

The insertion tool 10 may also include a handpiece 29 that is removably attached to the IOL cartridge 12 which may include a plunger case 31. The plunger case 31 may be a rigid, hollow, and tubular member that may be inserted into a handpiece 29. The plunger case 31 may be secured to the handpiece 29 via a flexible clip 38. The flexible clip 38 may extend from the plunger case 31 through an aperture 39 of the handpiece 29. It should be noted that various handpieces may be used with different types of IOL cartridges. The handpiece 29 may include an electrically powered or a non-electrically powered drive mechanism that may include a push rod 33 extending along a length of the handpiece 29. The push rod 33 may be movably disposed within the handpiece 29 and may be manually actuated via a rotatable knob 35, which may cooperate with a fluid or a resilient member such as a spring 37 or another actuation mechanism.

While the cap 14 is in the non-retracted position, the IOL 26 may be in an unfolded state, for example. A tip 19 of the cap 14 may include an aperture 17 to expose a nozzle (not shown) as the cap 14 is retracted, in a direction indicated by a directional arrow 23. In general, for the purposes of discussing and describing the various components and features of the handpiece 29 and the IOL cartridge 12, reference to a proximal end or direction may refer to a direction more towards an end of the handpiece 29 comprising the rotatable knob 35, according to the directional arrow 23. Likewise, reference to a distal end or direction may refer to a direction more towards an end of the IOL cartridge 12 comprising the tip 19, according to a directional arrow 27.

Figure 2:
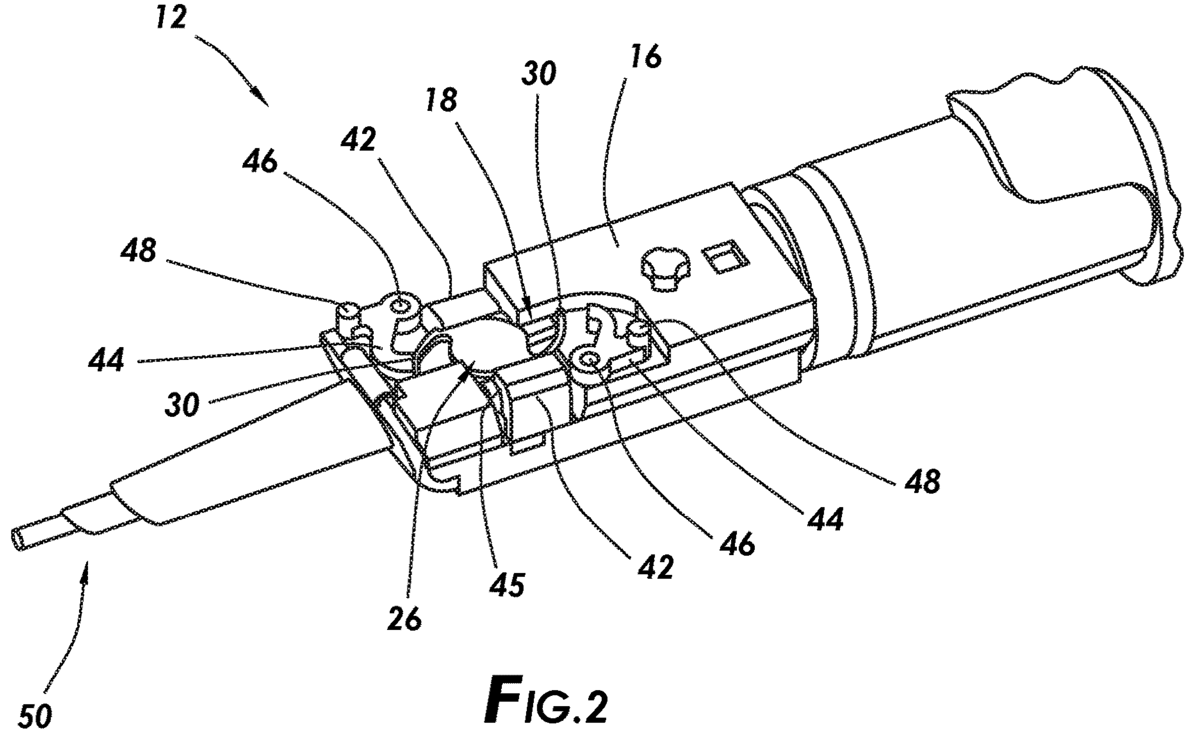
FIG. 2 illustrates a cutaway top perspective view of the IOL cartridge, in accordance with some embodiments of the present disclosure.

FIG. 2 is a cutaway top perspective view of the IOL cartridge 12 of FIG. 2 while the cap 14 (shown on FIG. 1) is in the non-retracted position, in accordance with particular embodiments of the present disclosure. In the illustrated embodiment, the cap 14 is not depicted to allow viewing of internal components beneath the cap 14 of the IOL cartridge 12.

The interior housing 16 may include the compartment 18. The compartment 18 may include one or more mechanisms or actuators for engaging with the IOL 26 in order to fold, splay, straighten, or otherwise manipulate the IOL 26. For example, a folding mechanism may include edge rollers 42 pivotably attached to the interior housing 16. The interior housing 16 may also include compression arms 44 that are also pivotably disposed within the interior housing 16 via pins 46 which extend vertically through the compression arms 44 into the housing 16 to allow rotation (e.g., in a lateral direction) of the compression arms 44. The compression arms 44 may include projections 48 that may extend upward to contact internal ramps (not shown) of the cap 14.

The IOL 26 may be disposed at a center of the interior housing 16 within the compartment 18 and between the compression arms 44 and the edge rollers 42. The IOL 26 may be preloaded and held in place within grooves 45 of the edge rollers 42. The edge rollers 42, upon actuation (i.e., retraction of the cap 14), rotate inward and downward (e.g., vertical rotation) to fold the IOL 26. Simultaneously, upon actuation, the compression arms 44 laterally rotate inward to compress the haptic extensions 30. Once compressed and folded, the IOL 26 is ready for delivery into an eye. The IOL cartridge 12 may also include a nozzle 50 that is in fluid communication with the compartment 18. The IOL 26 may be delivered through the nozzle 50.

Figure 3:
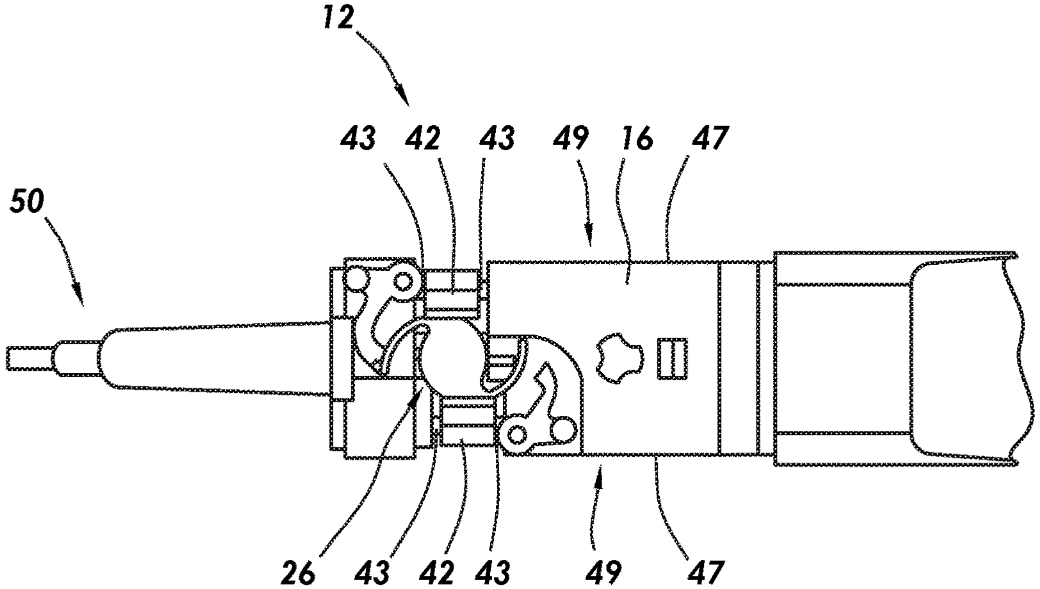
FIG. 3 illustrates a cutaway top view of the IOL cartridge, in accordance with some embodiments of the present disclosure.

FIG. 3 is a cutaway top view of the IOL cartridge 12 of FIG. 2 in the non-retracted position, in accordance with particular embodiments of the present disclosure. In the illustrated embodiment, the cap 14 (shown on FIG. 1) is not depicted to allow viewing of internal components beneath the cap 14 of the IOL cartridge 12. Pins 43 extend from the edge rollers 42 into the interior housing 16, thereby enabling rotation of the edge rollers 42, upon retraction of the cap 14. Upon depression, the cap 14 may axially move along lateral portions 47 that extend longitudinally along an exterior 49 of the interior housing 16. As previously noted, retraction of the cap 14 causes rotation of the edge rollers 42 and the compression arms 44, thereby folding and compressing the IOL 26 for delivery through the nozzle 50.

Figure 4:
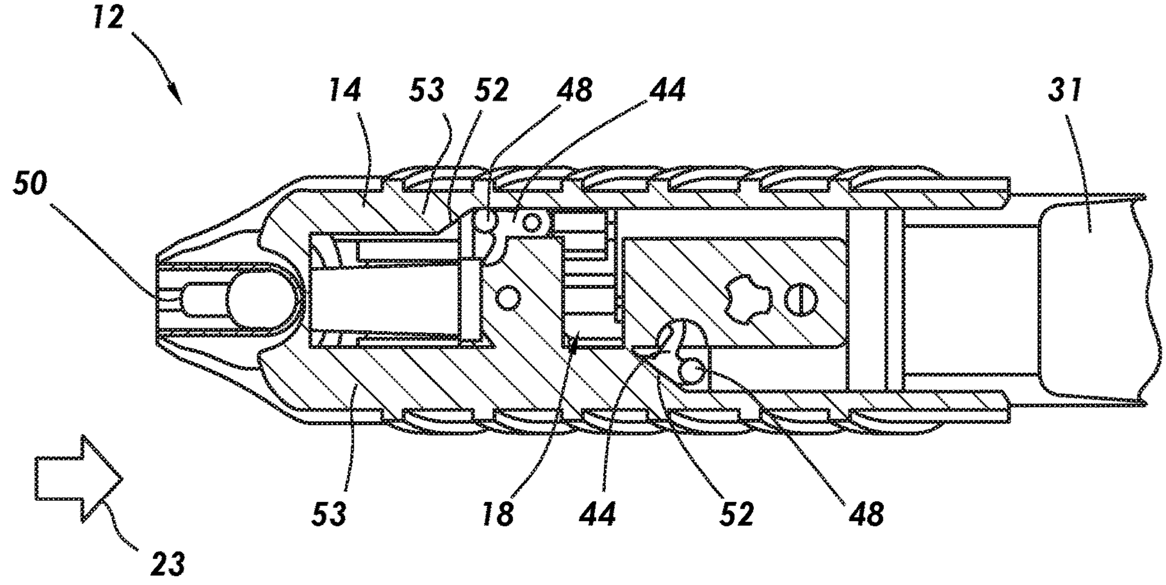
FIG. 4 illustrates a cutaway top view of the IOL cartridge with the retractable cap in an initial non-retracted position, in accordance with some embodiments of the present disclosure.

FIG. 4 illustrates a cutaway top view of an IOL cartridge 12 with a cap 14 in the non-retracted position, in accordance with particular embodiments of the present disclosure. The cap 14 is in the initial non-retracted position to provide protective coverage for the nozzle 50 and to maintain the IOL 26 (shown on FIG. 1) in a non-folded state during storing and/or shipping of the IOL cartridge 12.

The plunger case 31 may extend from an end of the IOL cartridge 12 that is opposite to the nozzle 50, as illustrated. The cap 14 may include internal ramps 52 that are aligned with the projections 48 of the compression arms 44. The internal ramps 52 may extend inward from lateral portions 53 of the cap 14. The internal ramps 52 may be configured to guide the projections 48 along the internal ramps 52, as the cap 14 is retracted (indicated by the directional arrow 23). The compression arms 44 may rotate inward (e.g., lateral rotation) as the cap 14 is advanced and the projections 48 move along the internal ramps 52, thereby compressing the haptic extensions 30 (e.g., shown on FIG. 1).

Figure 5:
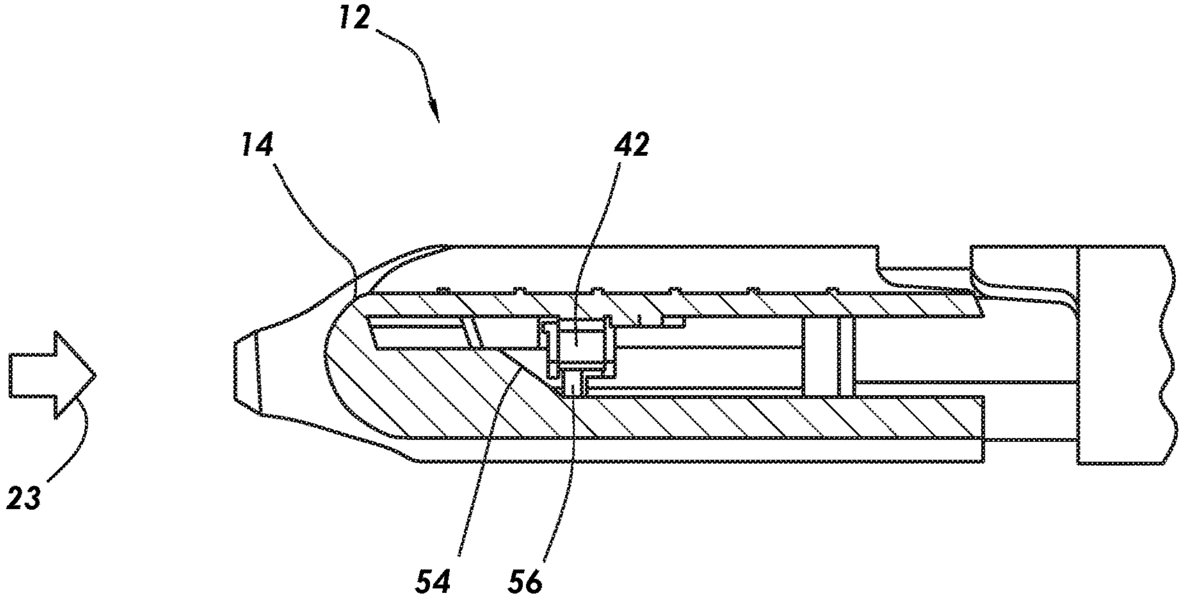
FIG. 5 illustrates a cutaway side view of the IOL cartridge with the retractable cap in the initial non-retracted position, in accordance with some embodiments of the present disclosure.

FIG. 5 illustrates a cutaway side view of the IOL cartridge 12 with the cap 14 in the non-retracted position, in accordance with particular embodiments of the present disclosure. Although not illustrated, an opposite side of the cap 14 is configured similarly to the side that is depicted. The cap 14 is in the initial non-retracted position. The cap 14 may include an internal ramp 54 that is aligned with a lower portion 56 of the edge roller 42. The internal ramp 54 may extend upward and may be configured to receive and lift or raise the lower portion 56 of the edge roller 42, as the cap 14 is retracted (indicated by the arrow 23). As the lower portion 56 of the edge roller 42 is contacted by the internal ramp 54, the lower portion 56 may be pushed upward due to the inclined surface of the internal ramp 54, as the cap 14 is further retracted or moved in the direction indicated by the arrow 23. As the lower portion 56 of the edge roller 42 is raised, the edge roller 42 may rotate vertically to fold the IOL 26 (shown on FIG. 1). Therefore, as the cap 14 is retracted (indicated by the arrow 23), both internal ramps 54 (one on either side of the cap 14) may contact the lower portions 56 of the edge rollers 42 and vertically rotate the edge rollers 42, thereby folding the IOL 26.

Figure 6:
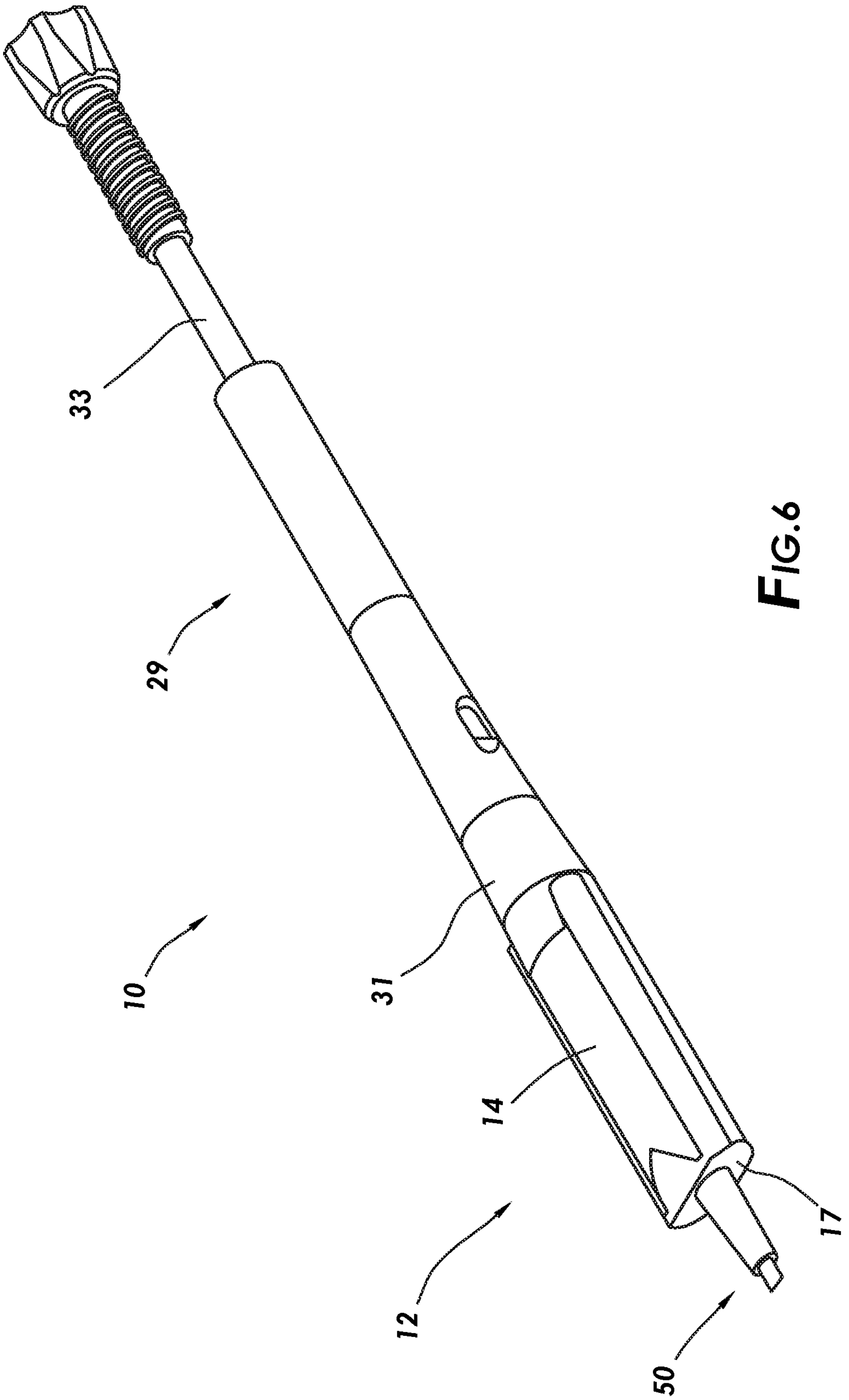
FIG. 6 illustrates a top perspective view of the insertion tool including the IOL cartridge with the retractable cap in a retracted position, in accordance with some embodiments of the present disclosure.

FIG. 6 illustrates a top perspective view of the insertion tool 10 including the IOL cartridge 12 with the cap 14 in a retracted position, in accordance with some embodiments of the present disclosure. While the cap 14 is in the retracted position, the IOL 26 (not shown) is in a folded and compressed state. In the illustrated embodiment, the cap 14 has been retracted such that the nozzle 50 has passed through the aperture 17 of the cap 14, thereby exposing the nozzle Upon depression of the push rod 33 the IOL 26 may be advanced from the IOL cartridge 12.

Figure 7:
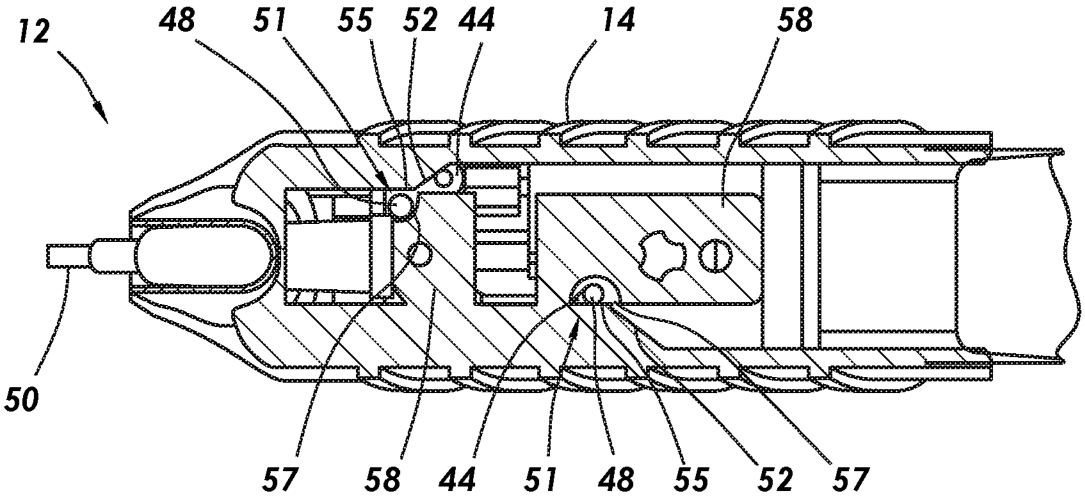
FIG. 7 illustrates a cutaway top view of an IOL cartridge with the retractable cap in a retracted position, in accordance with some embodiments of the present disclosure.

FIG. 7 illustrates a cutaway top view of the IOL cartridge 12 with the cap 14 in the retracted position, in accordance with particular embodiments of the present disclosure. In the illustrated embodiment, the cap 14 is in the retracted position to expose the nozzle 50. In this retracted position, the internal ramps 52 have been advanced and the projections 48 of the compression arms 44 have moved along the internal ramps 52 to flat portions 51 of the cap 14. The flat portions 51 are adjacent to apexes 55 of the internal ramps 52. The projections 48 are locked in place within recesses 57 that may be positioned in center portions 58 of the cap 14. The recesses 57 are adjacent to the flat portions 51 and the apexes 55, while the cap 14 is in the retracted position. In this retracted position, the compression arms 44 are laterally rotated inward and the haptic extensions 30 (shown on FIG. 1) are compressed.

Figure 8:
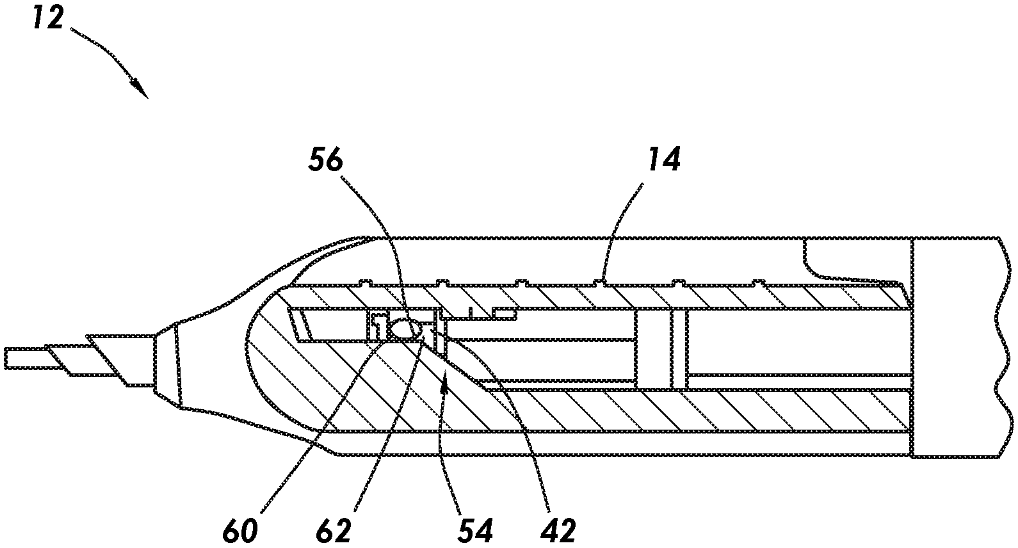
FIG. 8 illustrates a cutaway side view of the IOL cartridge with the retractable cap in the retracted position, in accordance with some embodiments of the present disclosure.

FIG. 8 illustrates a cutaway side view of the IOL cartridge 12 with the cap 14 in a retracted position, in accordance with particular embodiments of the present disclosure. As previously noted, the opposite side of the cap 14 may be configured similarly to the side that is illustrated. In the illustrated embodiment, the cap 14 is in the retracted position and the IOL 26 (not shown) is in a folded state. The internal ramp 54 has been advanced and the lower portion 56 of the edge roller 42 has been vertically raised and rotated and is positioned on a flat portion of the cap 14 that may be adjacent to an apex 62 of the internal ramp 54. Upon advancement of the internal ramps 54 of the cap 14, the lower portions 56 of the edge rollers 42 are vertically rotated and positioned on the flat portions 60, and the IOL 26 is in a folded state.

Figure 9:
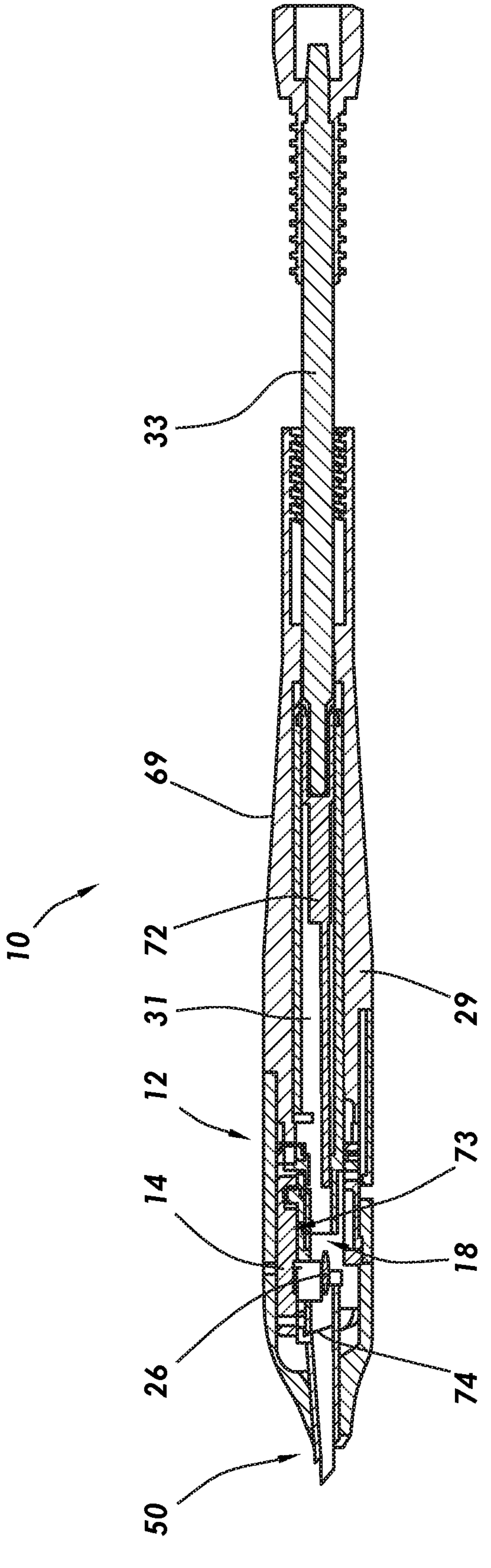
FIG. 9 illustrates a side cross-sectional view of an IOL cartridge removably attached to a handpiece.

FIG. 9 illustrates a side cross-sectional view of the insertion tool 10 that includes the IOL cartridge 12 removably attached to the handpiece 29 in accordance with particular embodiments of the present disclosure. In the illustrated embodiment, the cap 14 is retracted and the nozzle 50 is exposed. An interior portion 73 of the cap 14 is exposed to the compartment 18. The plunger case 31 may be disposed within a housing 69 of the handpiece 29 and secured therein via the flexible clip 38 (shown on FIG. 1). The plunger case 31 is in fluid communication with the compartment 18. A plunger 72 may be movably disposed within the plunger case 31. The plunger 72 may be an elongated rigid member extending lengthwise within the plunger case 31. The push rod 33 of the handpiece 29 may be actuated to advance the plunger 72 forward to deliver the IOL 26, in the folded and compressed state, from the compartment 18 through a passage 74 and the nozzle 50, and into a patient's eye. The passage 74 may extend from the compartment 18 and through the nozzle 50. After delivery of the IOL 26, the nozzle 50 may be removed from the patient's eye, and the handpiece 29 may be pulled from the IOL cartridge 12 to disengage the IOL cartridge 12 from the handpiece 29. The flexible clip 38 (shown on FIG. 1) may be depressed to unlock the IOL cartridge 12 from the handpiece 29. The used IOL cartridge 12 may then be disposed.

With reference to FIGS. 1-9, an exemplary technique for assembling the IOL cartridge 12 (e.g., shown on FIG. 1) to a handpiece (e.g., the handpiece 29 shown on FIG. 1) to form the insertion tool 10 (e.g., shown on FIG. 1) in accordance with particular embodiments of the present disclosure is described as follows.

First, the plunger case 31 of the IOL cartridge 12 with the cap 14 in a non-retracted position (e.g., see FIG. 1) may be inserted into the handpiece 29 (e.g., see FIG. 1) thereby securing (e.g., via the flexible clip 38 shown on FIG. 1) the IOL cartridge 12 to the handpiece 29 to form the insertion tool 10. Then, the cap 14 may be retracted to expose the nozzle 50 (e.g., see FIG. 6). As the cap 14 is retracted (e.g., see FIGS. 7 and 8), the IOL 26 may be folded and compressed (e.g., see FIGS. 7 and 8). As previously mentioned, in additional or alternative embodiments, in addition to or instead of folding the IOL 26, the cap 14 and internal housing 16 of the IOL cartridge 12 may be configured such that retraction of the cap 14 causes one or more portions of the IOL 26, such as the haptic extensions 30, to be straightened or splayed. Upon actuation of the push rod 33 (e.g., see FIG. 1), the plunger 72 advances forward to deliver the IOL 26 from the compartment 18 through the nozzle 50 (e.g., see FIG. 9).

To disassemble the insertion tool 10 after delivery of the IOL 26, the IOL cartridge 12 may be pulled out from the handpiece 29 thereby sliding the plunger case 31 out from the handpiece 29 to form a separate IOL cartridge 26 and a separate handpiece 29.

Figure 10A:
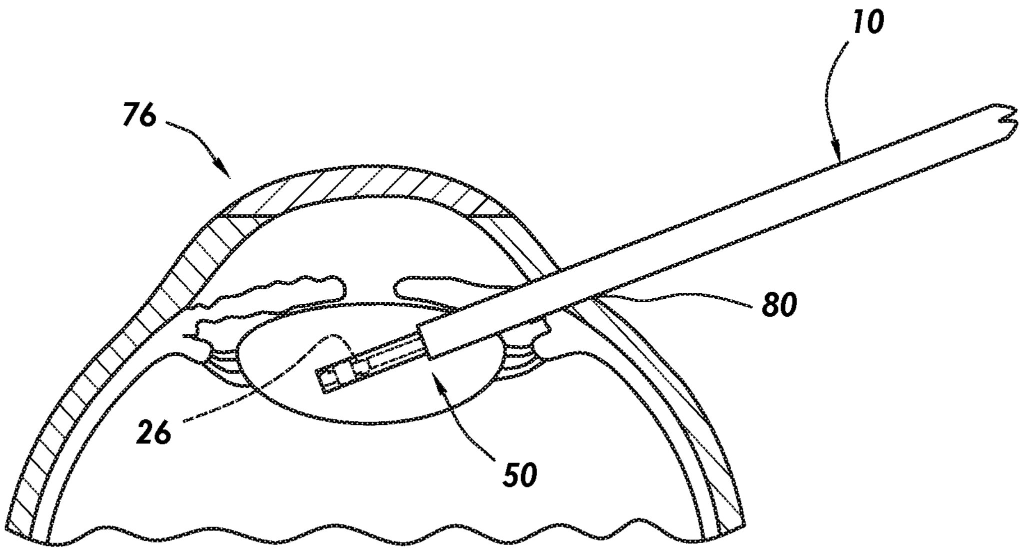
FIGS. 10A and 10B illustrate implantation of an IOL in accordance with some embodiments of the present disclosure.
Figure 10B:
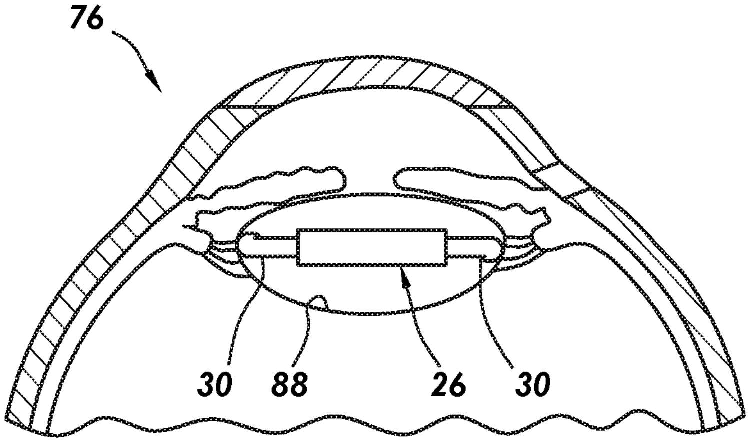

FIGS. 10A and 10B illustrate an exemplary technique for implantation of the IOL 26 into an eye 76 of a patient in accordance with particular embodiments of the present disclosure. FIG. 10A illustrates an incision 80 that may be made in the eye 76 by a surgeon. For example, the incision 80 may be made through the sclera of the eye 76. The incision 80 may be a suitable width or length. Without limitation, the suitable width and/or length may be less than 3 millimeters, and in some instances may be less than 2 millimeters. After the incision 80 is made, the nozzle 50 of the insertion tool 10 may be inserted through the incision 80 into an interior portion of the eye 76. The insertion tool 10 may be actuated to dispense the IOL 26 into a capsular bag 88 of the eye 76, as shown on FIG. 10B.

The IOL 26 may be delivered in a folded (or rolled configuration) and allowed to unfurl after ejection from the insertion tool 10. Upon dispensation, the IOL 26 should unfurl and settle within the capsular bag 88 of the eye 76, as shown on FIG. 10B. The haptic extensions 30 may be manipulated, for example, to engage an equator of the capsular bag 88. The haptic extensions 30 may engage the capsular bag 88 to secure the IOL 26 in the capsular bag 88.

Use of the methods and systems described herein may provide numerous benefits and advantages over other IOL delivery systems. For example, folding or other manipulation of the IOL may be streamlined. The integrated functionality of the folding or other manipulation of the IOL 26 with the retraction of the cap 14 of the IOL cartridge 12 may ensure that the IOL insertion tool 10 is used correctly and may guard against potential user errors. For example, in order to expose the nozzle 50 of the IOL cartridge 12, the cap 14 must first be retracted, thus causing the IOL 26 to be folded and put into a proper configuration for delivery. This integrated functionality of the retractable cap 14 may thus ensure that a proper sequence of steps for preparing, configuring, and delivering an IOL are followed, and therefore may guard against premature delivery or ejection of the IOL 26 prior to proper folding or other configuring.

Additionally, the interchangeable utilization between different drive mechanisms and the preloaded IOL cartridge offers a simplified and uniform process for pairing drive mechanisms to preloaded IOL cartridges. Thus, a variety of handpieces employing different types of drive mechanisms may be used with each of numerous different types of IOL cartridges, and therefore different types of IOLs. For example, a user may readily select between multiple types of drive mechanisms he or she wishes to use depending on the type of IOL and/or the type of IOL cartridge. Additionally, while one user may prefer to use a first type of drive mechanism handpiece for a given IOL cartridge, a different user may have the option of using a second type of drive mechanism handpiece for the same given type of IOL cartridge. Importantly, by allowing for a common, or standard interface for securing the handpieces to the IOL cartridges, the user experience of securing a handpiece to an IOL cartridge may be substantially the same, regardless of the type of drive mechanism or type of IOL cartridge, and thus IOL, being used, which may also increase ease-of-use for an operator as well as streamline IOL delivery procedures.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An intraocular lens (IOL) cartridge, the IOL cartridge comprising:
- an interior housing comprising a compartment configured to receive an IOL;
- a plurality of compression arms pivotably attached within the interior housing, wherein:

the plurality of compression arms are pivotably attached within the interior housing via pins that extend vertically through the plurality of compression arms and into the interior housing; and
- a cap configured to at least partially enclose the interior housing and be retracted from a first position to a second position to actuate the plurality of compression arms, wherein actuation of the compression arms causes manipulation of the IOL for delivery.

2. The IOL cartridge of claim 1, wherein the plurality of compression arms are configured to rotate laterally inward upon retraction of the cap from the first position to the second position to compress one or more haptics of the IOL.

3. The IOL cartridge of claim 1, further comprising:
- edge rollers pivotably attached to the interior housing.

4. The IOL cartridge of claim 3, wherein the cap comprises a first set of internal ramps configured to contact and rotate the edge rollers to fold the IOL upon retraction of the cap from the first position to the second position.

5. The IOL cartridge of claim 4, wherein the cap comprises a second set of internal ramps configured to contact and rotate the compressions arms to compress one or more haptics of the IOL upon retraction of the cap from the first position to the second position.

6. The IOL cartridge of claim 5, wherein the plurality of compression arms include projections that extend upward to contact the second set of internal ramps.

7. The IOL cartridge of claim 6, wherein the projections are guided by the second set of internal ramps to contact and rotate the plurality of compression arms to compress the IOL upon retraction of the cap from the first position to the second position.

8. An intraocular lens (IOL) cartridge, the IOL cartridge comprising:

a nozzle;

an interior housing comprising a compartment configured to receive an IOL, the compartment in fluid communication with the nozzle;

a plurality of compression arms pivotably attached within the interior housing; and a cap configured to at least partially enclose the interior housing, the cap further configured to be retracted from a first position to a second position to actuate the plurality of compression arms and expose the nozzle, wherein actuation of the plurality of compression arms causes manipulation of the IOL for delivery.

9. The IOL cartridge of claim 8, wherein the plurality of compression arms are pivotably attached within the interior housing via pins that extend vertically through the plurality of compression arms and into the interior housing.

10. The IOL cartridge of claim 8, wherein the plurality of compression arms are configured to rotate laterally inward upon retraction of the cap from the first position to the second position to compress one or more haptics of the IOL.

11. The IOL cartridge of claim 8, further comprising:

edge rollers pivotably attached to the interior housing.

12. The IOL cartridge of claim 11, wherein the cap comprises a first set of internal ramps configured to contact and rotate the edge rollers to fold the IOL upon retraction of the cap from the first position to the second position.

13. The IOL cartridge of claim 12, wherein the cap comprises a second set of internal ramps configured to contact and rotate the compressions arms to compress one or more haptics of the IOL upon retraction of the cap from the first position to the second position.

14. The IOL cartridge of claim 13, wherein the plurality of compression arms include projections that extend upward to contact the second set of internal ramps.

15. The IOL cartridge of claim 14, wherein the projections are guided by the second set of internal ramps to contact and rotate the plurality of compression arms to compress the IOL upon retraction of the cap from the first position to the second position.

16. An intraocular lens (IOL) cartridge, the IOL cartridge comprising:

a housing comprising a compartment configured to receive an IOL;

a folding mechanism comprising a pair of compression arms pivotably disposed within the housing, wherein:

the pair of compression arms are pivotably attached within the housing via pins that extend vertically through the pair of compression arms and into the housing; and a removable cap configured to at least partially surround the compartment, the removable cap further configured to be retracted from a first position to a second position to actuate the folding mechanism of the housing to manipulate the IOL for delivery, wherein:

the pair of compression arms are configured to laterally rotate inward upon actuation to compress one or more haptics of the IOL.

17. The IOL cartridge of claim 16, wherein the removable cap comprises a set of internal ramps configured to engage the pair of compression arms as the cap is retracted from the first position to the second position.

18. The IOL cartridge of claim 17, wherein the set of internal ramps is configured to contact projections on the pair of compression arms upon retraction of the removable cap to rotate the pair of compression arms.

19. The IOL cartridge of claim 18, wherein the cap comprises recesses to receive and secure the projections on the pair of compression arms upon retraction of the removable cap.

* * * * *